(12) United States Patent
Cleland et al.

(10) Patent No.: US 7,582,311 B1
(45) Date of Patent: Sep. 1, 2009

(54) INJECTION VEHICLE FOR POLYMER-BASED FORMULATIONS

(75) Inventors: Jeffrey L. Cleland, San Carlos, CA (US); Xanthe M. Lam, South San Francisco, CA (US); Franklin Okumu, Oakland, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/687,951

(22) Filed: Oct. 13, 2000

Related U.S. Application Data

(60) Provisional application No. 60/159,739, filed on Oct. 15, 1999.

(51) Int. Cl.
*A61K 9/14* (2006.01)
*A61K 38/00* (2006.01)

(52) U.S. Cl. .................. 424/489; 424/488; 424/490; 424/497; 514/2; 514/8; 514/12; 514/54; 530/324

(58) Field of Classification Search ............. 424/488, 424/489, 490, 497; 514/2, 8, 12, 54; 536/551; 530/324
See application file for complete search history.

(56) References Cited

U.S. PATENT DOCUMENTS

| | | | |
|---|---|---|---|
| 3,523,906 A | 8/1970 | Vranchen et al. | |
| 3,691,090 A | 9/1972 | Kitajima et al. | |
| 3,737,337 A | 6/1973 | Schnoring et al. | |
| 4,389,330 A | 6/1983 | Tice et al. | |
| 4,652,441 A | 3/1987 | Okada et al. | |
| 4,816,440 A | 3/1989 | Thomson et al. ............. | 514/12 |
| 4,935,237 A | 6/1990 | Higgins et al. ........... | 424/94.64 |
| 4,937,270 A | 6/1990 | Hamilton et al. ............ | 514/777 |
| 5,017,229 A | 5/1991 | Burns et al. ................. | 106/162 |
| 5,019,400 A | 5/1991 | Gombotz et al. | |
| 5,137,875 A * | 8/1992 | Tsunenaga et al. ............ | 514/21 |
| 5,204,382 A | 4/1993 | Wallace et al. | |
| 5,288,502 A * | 2/1994 | McGinity et al. ........... | 424/484 |
| 5,416,071 A * | 5/1995 | Igari et al. ...................... | 514/8 |
| 5,527,893 A | 6/1996 | Burns et al. ................... | 514/53 |
| 5,643,605 A | 7/1997 | Cleland et al. .............. | 424/489 |
| 5,681,814 A | 10/1997 | Clark et al. ................... | 514/12 |
| 5,783,556 A | 7/1998 | Clark et al. ................... | 514/4 |
| 5,804,557 A | 9/1998 | Cleland et al. ................ | 514/12 |
| 5,851,989 A | 12/1998 | Chamow et al. ................ | 514/8 |
| 5,879,673 A | 3/1999 | Thomas ..................... | 424/85.1 |
| 5,985,354 A * | 11/1999 | Mathiowitz et al. ........ | 427/2.21 |
| 6,113,947 A * | 9/2000 | Cleland et al. .............. | 424/489 |
| 6,197,326 B1 * | 3/2001 | Suzuki et al. ............... | 424/426 |
| 2007/0098736 A1 | 5/2007 | Cleland et al. | |

FOREIGN PATENT DOCUMENTS

| | | | |
|---|---|---|---|
| CA | 2178902 | | 6/1995 |
| CA | 2289196 | | 11/1998 |
| EP | 0263490 | * | 6/1987 |
| EP | 0535 937 A1 | | 9/1992 |
| EP | 0 633 020 | | 1/1995 |
| FR | 2 778 847 | | 11/1999 |
| FR | 27778847 | * | 11/1999 |
| WO | WO 91/05544 | | 5/1991 |
| WO | WO-95/16464 A1 | | 6/1995 |
| WO | WO-95/29664 A1 | | 11/1995 |
| WO | WO-98/51348 A2 | | 11/1998 |
| WO | WO-98/51348 A3 | | 11/1998 |
| WO | WO-01/28591 A2 | | 4/2001 |
| WO | WO-01/28591 A3 | | 4/2001 |

OTHER PUBLICATIONS

Aldrich Handbook of Fine Chemicals and Laboratory Equipment, Syringes section, p. T679.*
Aldrich Catalog (1996-1997), p. T515.*
Cleland, Jeffrey L., "Protein Delivery from Biodegradable Microspheres," *Protein Delivery: Physical Systems*, Chapter 1, pp. 1-43 (1997).
Johnson, OluFunmi L. et al., "The Stabilization and Encapsulation of Human Growth Hormone into Biodegradable Microspheres," *Pharmaceutical Research* 14:6:730-735 (1997).
Liesegang, Thomas J., "Viscoelastic Substances in Opthalmology" *Survey of Opthalmology* 34:4:268-293 (Jan./Feb. 1990).
Putney, S. et al., "Enhanced Anti-Tumor Effects with Microencapsulated c-myc Antisense Oligonucleotide," *Antisense & Nucleic Acid Drug Development*, vol. 9, pp. 451-458 (1999).
EP Communication in EP Application No. 00971986.5-2123 (Third Party Observation) dated Oct. 19, 2006 (5 pgs.).
Cowsar, D.R. et al. (1985). "Poly(lactide-co-glycolide) Microcapsules for Controlled Release of Steroids," Chapter 8 in *Methods in Enzymology*, 112:101-116.
Holland, S.J. et al. (1986). "Polymers for Biodegradable Medical Devices. 1. The Potential of Polyesters as Controlled Macromolecular Release Systems," *J. Controlled Release* 4:155-180.
Lewis, D.H. et al. (1990). Controlled Release of Bioactive Agents from Lactide/Glycolide Polymers, Chapter 1 in *Biodegradable Polymers as Drug Delivery Systems*, Marcel Dekker, Inc.:New York, NY, pp. 1-41.
Maulding, H.V. (1987). "Prolonged Delivery of Peptides by Microcapsules," *J. Controlled Release* 6:167-176.

(Continued)

*Primary Examiner*—Chih-Min Kam
(74) *Attorney, Agent, or Firm*—Morrison & Foerster LLP

(57) ABSTRACT

The invention provides injection vehicles suitable for administering particulate suspensions, such as polymer-based formulations, as well as associated pharmaceutical formulations, articles of manufacture, and kits. Other aspects of the invention included methods for producing and administering pharmaceutical formulations. The injection vehicles of the invention are superior to conventional injection vehicles in that they include a pseudoplastic composition that improves injectability, which facilitates delivery of the desired dose. The injection vehicles of the invention also allow the use of smaller-bore needles than are usually necessary to inject polymer-based formulations, reducing the pain associated with injection of such formulations.

44 Claims, No Drawings

OTHER PUBLICATIONS

Non-Final Office Action mailed Nov. 9, 2007, for U.S. Appl. No. 11/614,462, 9 pages.

Office Action mailed Aug. 13, 2007, for Canadian Patent Application No. 2,387,058, three pages.

Ogawa Y. et al. (Mar. 1988). "A New Technique to Efficiently Entrap Leuprolide Acetate into Microcapsules of Polylactic Acid of Copoly(Lactic/Glycolic) Acid," *Chem. Pharm. Bull.* 36(3):1095-1103.

Ogawa, Y. et al. (Jul. 1988). "In Vivo Release Profiles of Peuprolide Acetate from Microcapsules Prepared with Polylactic Acids or Copoly(Lactic/Glycolic) Acids and in Vivo Degradation of These Polymers," *Chem. Pharm. Bull.* 36(7):2576-2581.

Restriction Requirement mailed Jun. 25, 2007, for U.S. Appl. No. 11/614,462, 5 pages.

Sanders, L.M. et al. (Apr. 1986). "Prolonged Controlled-Release of Nafarelin, a Luteinizing Hormone-Releasing Hormone Analogue, From Biodegradable Polymeric Implants: Influence of Composition and Molecular Weight of Polymer," *J. Pharm. Sci.* 75(4):356-360.

Smith, K.L. et al. (Jan.-Apr. 1990). "Bioerodible Polymers for Delivery of Macromolecules," *Advanced Drug Delivery Reviews* 4(3):343-357.

\* cited by examiner

INJECTION VEHICLE FOR POLYMER-BASED FORMULATIONS

CROSS-REFERENCE TO RELATED APPLICATIONS

This application claims the benefit of U.S. Provisional Application No. 60/159,739 filed Oct. 15, 1999, entitled "INJECTION VEHICLE FOR POLYMER-BASED FORMULATIONS" and naming Jeffrey L. Cleland, Xanthe M. Lam and Franklin Okumu as inventors. This prior application is hereby incorporated by reference in its entirety.

FIELD OF THE INVENTION

The invention relates to injection vehicles for particulate suspensions, e.g., polymer-based formulations and associated pharmaceutical formulations and methods. In particular, the invention relates to injection vehicles, pharmaceutical formulations, and methods that allow the use of smaller-bore needles to inject particulate suspensions.

BACKGROUND OF THE INVENTION

Sustained-release delivery systems for therapeutic agents have received a considerable amount of attention in recent years. Examples include controlled-release injectable and oral formulations, transdermal patches, and implantable depot formulations. Such systems are of particular interest as a means of delivering therapeutic proteins.

When producing formulations of therapeutic proteins, it is important to preserve the physical, chemical, and biological properties of the protein. In contrast to lower molecular weight drugs, proteins typically have large globular structures, including secondary, tertiary, and in some cases, quaternary structural features that are important for biological activity. Furthermore, proteins have labile bonds and chemically reactive groups on their side chains which are susceptible to oxidation (methionine, tryptophan, histidine, tyrosine), deamidation (arginine, glutamine) or disulfide reduction or interchange (cysteine). In addition to preserving biological activity, it is particularly important to reduce or eliminate protein alterations that increase the protein's immunogenicity. Undesired immune responses can lead to safety concerns, and neutralizing antibody responses can limit the efficacy of subsequent treatments. Thus, the need to stabilize therapeutic proteins for long periods in a physiological environment has been an obstacle to the development of sustained-release protein delivery systems.

One way to stabilize drugs is to embed them in biodegradable polymeric microparticles (Maulding (1987), J. Controlled Release 6:167-176; Smith et al. (1990), Advanced Drug Delivery Reviews 4:343-357; Holland et al. (1986), J. Controlled Release 4:155-180; Lewis et al. (1990), Biodegradable Polymers as Drug Delivery Systems, pp. 1-41, Dekker, New York.) Studies using microparticles made from homo- and co-polymers of lactic and glycolic acid (PLGA polymers) have shown that these polymers hydrolyze to acid monomers (Maulding (1987), J. Controlled Release 6:167-176; Smith et al. (1990), Advanced Drug Delivery Reviews 4:343-357; Cower et al. (1985), Methods in Enzymology 112:101-116) and are chemically unreactive under the conditions used to prepare the microparticles. Such polymers can be produced in a range of molecular weights and monomer ratios which allows adjustment of the drug release rate to the particular application. PLGA polymers are non-immunogenic and non-toxic. These properties led to the selection of a PLGA polymer for use in the depot formulation of the luteinizing hormone releasing hormone (LHRH) agonist luprolide (Sanders et al. (1986), J. Pharm. Sci. 75:356-360; Ogawa et al. (1988), Chem. Pharm. Bull. 5:1095-1103; Ogawa et al. (1988), Chem. Pharm. Bull. 36:2576-2581). Johnson et al. (1997), Pharmaceutical Research 14:730-735, stabilized recombinant human growth hormone by forming a zinc-protein complex and encapsulated the complex in the solid state into PLGA microparticles (see also PCT Application No. PCT/US95/05511, Publication No. WO 95/29664).

Despite their advantages for stabilizing proteins, the administration of polymer-based drug formulations can be problematic. For example, the dose is limited by the amount of the formulation that can readily be suspended and injected. In formulations containing particles, aggregation or dilatancy can lead to clogging of the needle, making it difficult to administer the intended dose. In an effort to reduce agglomeration, excipients such as carboxymethylcellulose (CMC), dextran, or sorbitol have been included in the injection vehicle. Surfactants and salts have also been added in an effort to alter the particles' fluid properties. CMC, Tween™, and phosphate-buffered saline have been used in a vehicle for delivering a lupron depot formulation. However, the doses of this formulation are relatively small: 30-60 mg of microparticles each. In general, it is difficult to inject doses greater than 200 mg/mL of microparticles through a 21- or 23-gauge needle. Assuming a maximum subcutaneous dose of 1 mL, the maximum microparticle dose is 200 mg. The use of such large-bore needles increases the pain of injection, but the use of smaller bore needles further restricts the dose that can be delivered in a single injection.

An injection vehicle that enhanced the injectability of particulate suspensions, generally, and/or polymer-based drug formulations, in particular, would allow delivery of higher doses of drug and/or allow the use of smaller needles. These benefits would increase the feasibility of polymer-based formulations for a wider variety of therapeutic applications.

SUMMARY OF THE INVENTION

The present invention includes a fluid suitable for use in administering a particulate suspension by injection. This injection vehicle comprises a flexible molecule, such as hyaluronic acid or a derivative thereof, dissolved in a physiological buffer, such as saline.

The injection vehicle of the invention allows the injection of higher doses of particulate suspensions, such as polymer-based drug formulations, using smaller needles, than is possible using conventional injection vehicles.

The present invention also provides a pharmaceutical formulation including an effective amount of a biologically active agent in the injection vehicle of the invention. The biologically active agent can be in the form of particles, coated onto particles, dispersed within particles, or accompanied by particles in the injection vehicle. Such formulations can be employed to administer biologically active agents for prophylactic, therapeutic, or diagnostic applications.

In a preferred embodiment, the biologically active agent is a polypeptide dispersed within particles that provide sustained release of the polypeptide. The particles are, preferably, composed of a biocompatible polymer matrix, such as a poly(lactide-co-glycolide) matrix. Preferred formulations include, for example, a growth hormone, a hepatocyte growth factor (HGF), a vascular endothelial growth factor (VEGF), an anti-VEGF Fab, a glucagon-like peptide I (GLP-I), a nerve growth factor, or an insulin-like growth factor as the biologically active agent.

The present invention also encompasses methods for producing and administering the pharmaceutical formulations described herein. In a preferred embodiment, a pharmaceutical formulation according to the invention is administered by injection through a 23-gauge or smaller needle.

DETAILED DESCRIPTION OF THE INVENTION

Definitions

Terms used in the specification and claims are defined as set forth below unless otherwise specified.

The term "injection vehicle" refers to a fluid suitable for use in administering a drug by injection (e.g., subcutaneous, intramuscular, intravenous, etc.).

The term "pseudoplastic composition" refers to a composition having a viscosity that decreases with increasing shear rate. Shear is the friction that occurs when a plate is moved relative to another plate with a solution between them. Shear rate is the speed at which the plate is moved. Shearing also occurs when a viscous substance flows through a needle, and thus pseudoplasticity affects the ease with which such substances can be injected.

"Hyaluronic acid" is a large, branched mucopolysaccharide molecule with alternating beta (1-3) glucuronide and beta (1-4) glucosamide bonds. As used herein, the term "hyaluronic acid" refers to the form having the same structure as the naturally occurring molecule found in the extracellular matrix of vertebrate connective tissues.

A wide variety of chemical modifications of hyaluronic acid are possible. The term "hyaluronic acid derivative" is used herein to refer to a molecule having the hyaluronic acid "backbone" (i.e., the alternating glucuronide and glucosamide bonds) and one or more chemical groups not present in naturally occurring hyaluronic acid. For ease of discussion, hyaluronic acid and its various derivatives are collectively termed "hyaluronic acids." Exemplary hyaluronic acids include ester, amide and lactide derivatives. The formation of specific acyl derivatives of hyaluronic acid is described in U.S. Pat. No. 5,527,893. Further, water-insoluble hyaluronic acid derivatives are described in U.S. Pat. Nos. 5,017,229 and 4,937,270. Hyaluronic acid has been conjugated to polyethylene glycol, and such "pegylated" forms are also "hyaluronic acids," as this term is used herein. Hyaluronic acids in the form of esters or salts, which are termed "hyaluronates," are conveniently employed in the invention.

The molecular weight of hyaluronic acids vary and therefore references herein to the molecular weight of hyaluronic acids refer to average molecular weights.

Concentrations expressed as "percent by volume" or "% (v/v)" are calculated by dividing the volume of the component by the total volume of the composition.

Concentrations expressed as "percent by weight" or "% (w/w)" are calculated by dividing the weight of the component by the total weight of the composition.

Concentrations expressed as "percent weight per volume" or % (w/v) are calculated by dividing weight (e.g., in grams) by volume (e.g., in liters).

"Viscosity" is a measure of a solution's resistance to flow, typically in units of centistokes (cSt or cs).

"Physiological saline" is defined as a 0.9 percent (weight/volume) sodium chloride in water.

A "polymer-based formulation" is defined as a formulation in which a biologically active agent is dispersed within a polymeric matrix.

The term "polymeric matrix" refers to a discontinuous polymeric structure with one or more other materials and/or spaces dispersed throughout.

The term "biocompatible" refers to a material that can be introduced into the human body in the amounts described herein without significant adverse effects, such as toxicity or immunogenicity. If the material is degraded in vivo, the term also indicates a material whose in vivo degradation products also do not cause significant adverse effects.

The term "biodegradable" refers to compositions that degrade or erode in vivo to form smaller units. Degradation can result from any process occurring in vivo, including enzymatic, chemical, and physical processes.

A "blocked polymer" has blocked carboxyl end groups. Generally, the blocking group is derived from the polymerization initiator and is typically an alkyl radical. An "unblocked polymer" has free carboxyl end groups.

The term "microparticles" is used herein to refer to particles having a maximum dimension (i.e., length or diameter) of less than about one millimeter. Microparticles that are substantially spherical and/or ellipsoidal are termed "microspheres."

A "biologically active agent" is defined as an agent having an in vivo activity, typically an activity that confers therapeutic, prophylactic, and/or diagnostic utility.

The terms "proteins" and "polypeptides" are used interchangeably herein.

The term "effective amount" describes an amount of a biologically active agent that produces an in vivo activity.

The term "aseptic processing" describes a process of sterilization that involves the sterilization of individual components used in a process or product, followed by processing and packaging activities carried out under aseptic conditions. A variety of conventional methods are used in aseptic processing, depending upon the physical characteristics of the product, its container, and the closure. Exemplary methods include filtration (liquid forms), dry heat-sterilization (glass components), pressurized steam (rubber components), and radiation and/or treatment with ethylene oxide (plastic components).

The term "terminal sterilization" describes a process whereby a drug product, which may or may not be presterilized, is filled and sealed in a container and then subjected to final sterilization. A number of techniques can be used in terminal sterilization and include, for example, radiation and autoclaving.

Injection Vehicle

The invention provides an injection vehicle comprising a pseudoplastic composition. The pseudoplastic composition provides improved injectability, compared with conventional injection vehicles, and is therefore particularly useful for injecting suspensions of particles, such as, for example, polymer-based formulations. Pseudoplastic compositions according to the invention are generally solutions of flexible molecules that deform to an ellipsoid conformation when exposed to shear forces and tend to become aligned in the direction of flow with increasing shear rate. Flexible molecules suitable for use in the present invention are typically, large branched polymeric molecules. Exemplary flexible molecules include hyaluronic acid, hyaluronic acid derivatives, and combinations thereof. Hyaluronic acid is preferred and is conveniently employed in the form of sodium hyaluronate.

Considerations affecting the selection of pseudoplastic compositions include viscosity, molecular weight, and pH.

Pseudoplastic compositions suitable for use in the invention are generally viscous enough to allow the polymer component of polymer-based formulations to remain suspended in the injection vehicle during injection. Dynamic viscosities can range from about 1,000 to about 500,000 centistokes (cSt) at a shear rate of l/second at 25° C. and are preferably in the range of about 1,000 to about 100,000 cSt, and more preferably in the range of about 2,000 to about 65,000 cSt.

The viscosity of a solution containing a flexible molecule is a composite function of molecular weight and concentration, as well as the temperature and solvent used. Specifically, viscosity increases with increasing molecular weight and increasing concentration. Flexible molecules suitable for use in the pseudoplastic composition of the invention generally have average molecular weights in the range of about $0.5 \times 10^5$ to about $5 \times 10^6$ Daltons although molecules of higher or lower average molecular weight can also be employed. Preferred average molecular weights for hyaluronic acids useful in the invention are between about $2 \times 10^5$ and about $5 \times 10^6$ Daltons.

The concentration of flexible molecules is generally between about 0.01 percent to about 10.0 percent weight per volume (w/v), although one skilled in the art appreciates that as average molecular weight increases, the concentration needed to achieve a particular viscosity decreases. Hyaluronic acids in the preferred size range described above are conveniently employed at a concentration between about 0.01 percent to about 3 percent (w/v), preferably between about 0.1 percent to about 1 percent (w/v), and more preferably less than 0.8 percent (w/v).

The pH of the pseudoplastic composition should generally be close to the physiologic norm of approximately 7.0. Preferred pseudoplastic compositions have a pH in the range of about 5.0 to 7.8.

The pseudoplastic composition can include any solvent capable of dissolving a flexible molecule, as described above, wherein the resulting solution has a suitable viscosity and pH for use in the invention. One skilled in the art can readily select a suitable solvent for a particular flexible molecule. Aqueous solvents are preferred, and examples include physiological buffers (such as physiological phosphate buffer) and physiological saline.

The pseudoplastic composition of the present invention is generally substantially free of endotoxin, exotoxin, fungi, precipitates, and the like, which can cause adverse reactions in the recipient. Sterilization of the composition can be achieved by acetic processing or terminal sterilization, using any conventional sterilization technique suitable for the composition. One skilled in the art can readily identify a sterilization technique suitable for a given composition.

Pharmaceutical Formulations

Pharmaceutical formulations of the invention comprise the injection vehicle of the invention, particles, and a biologically active agent. The particles and the biologically active agent can be a single component (i.e., the biologically active agent can be in particulate form) or two different components. Examples of the latter include embodiments in which the biologically active agent is coated on, or dispersed within, the particles. Preferred embodiments employ microparticles made up of a polymeric matrix having a biologically active agent dispersed therein. The concentration of particulate/biologically active agent component(s) depends on the desired dose and the maximum amount of the component(s) that can be injected. For example, polymeric microparticles including a biologically active agent dispersed therein are generally employed at concentrations between about 1 mg/mL and about 500 mg/mL and more preferably between about 50 mg/mL to about 150 mg/mL.

In polymer-based formulations, the polymer that forms the polymeric matrix is a biocompatible polymer that can be biodegradable or non-biodegradable, a mixture of biodegradable and non-biodegradable polymers, or a copolymer comprising biodegradable and non-biodegradable units. Suitable biocompatible, biodegradable polymers include, for example, poly(lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, block copolymers of polyethylene glycol and lactide or glycolide, and blends and copolymers thereof.

Biocompatible, non-biodegradable polymers suitable for pharmaceutical compositions of the invention include, for example, non-biodegradable polyacrylates, polymers of ethylene-vinyl acetates and other acyl-substituted cellulose acetates, non-degradable polyurethanes, polystyrenes, polyvinyl chloride, polyvinyl fluoride, poly(vinyl imidazole), chlorosulphonate polyolefins, polyethylene oxide, and blends and copolymers thereof.

The polymer can be blocked, unblocked, or a blend of blocked and unblocked polymers.

Suitable molecular weights for polymers used in the invention can be determined by a person of ordinary skill in the art taking into consideration factors such as the desired polymer degradation rate, and physical properties such as mechanical strength. Typically, polymer molecular weight ranges from about 2,000 Daltons to about 2,000,000 Daltons.

In a preferred embodiment, the polymer is a biodegradable polymer or copolymer. In a more preferred embodiment, the polymer is a poly(lactide-co-glycolide) (PLGA) with a lactide:glycolide ratio of about 1:1 and a molecular weight of about 5,000 Daltons to about 70,000 Daltons. In an even more preferred embodiment, the PLGA used in the present invention has a molecular weight of about 5,000 Daltons to about 42,000 Daltons.

Examples of therapeutic and/or prophylactic biologically active agents suitable for use in the invention include polypeptides, such as hormones, antigens, growth factors, etc.; polynucleotides, such as DNA or RNA to be expressed or antisense DNA or RNA molecules; and small molecules, such as antibiotics, steroids, decongestants, neuroactive agents, anesthetics, sedatives, and the like. Examples of suitable diagnostic and/or therapeutic biologically active agents include radioactive isotopes and radiopaque agents.

Examples of specific polypeptides that can be employed in pharmaceutical formulations according to the invention include cytokines and their receptors, as well as chimeric proteins comprising cytokines or their receptors, such as, for example, tumor necrosis factor alpha and beta, their receptors (TNFR-1; Gray et al. (1990), Proc. Natl. Acad. Sci. USA 87:7380-7384; and TNFR-2; Kohno et al. (1990), Proc. Natl. Acad. Sci. USA 87:8331-8335), and their derivatives; renin; a growth hormone, such as human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors, such as factor VIIIC, factor IX, tissue factor, and von Willebrand's factor; anti-clotting factors such as Protein C; atrial natriuretic factor; lung surfactant; plasminogen activators, such as tissue-type plasminogen activators and urokinases; bombesin; thrombin; hemopoietic growth factor; enkephalinase; RANTES (regulated on activation normally T-cell expressed and secreted); human macrophage inflammatory protein (MIP-1-alpha); a serum albumin, such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); anti-VEGF Fab, glucagon-like peptide I (GLP-I); receptors for hormones or growth factors; hepatocyte growth factor (HGF); integrin; protein A or D; rheumatoid factors; a neurotrophic factor, such as bone-derived neurotrophic factor (BDNF), neurotrophin-3, -4, -5, or -6 (NT-3, NT-4, NT-5, or NT-6), or a nerve growth factor, such as NGF-β; platelet-derived growth factor (PDGF); fibroblast growth factor, such as aFGF and bFGF; epidermal growth factor (EGF); transforming growth factor (TGF), such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-1); insulin-like growth factor binding proteins; CD proteins such as CD-3, CD-4, CD-8, and CD-19; erythrbpoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), such as IL-1 to IL-10; superoxide dismutase; T-cell receptors; surface membrane proteins; decay accelerating factor; viral antigens, such as, for example, the HIV-I envelope glycoproteins, gp120, gp160 or fragments thereof; transport proteins; homing receptors; addressins; regulatory proteins; antibodies, and portions thereof, such as Fab fragments; and chimeric proteins, such as immunoadhesins.

A pharmaceutical formulation according to the invention may also contain more than one biologically active agent, for instance, two different polypeptides.

As discussed above, the biologically active agent can be employed in the form of particles. Such particles can include, for example, crystalline particles, non-crystalline particles, freeze-dried particles, lyophilized particles, and combinations thereof. The particles may contain only the biologically active agent or may also contain a stabilizing agent and/or other excipient. The particles can be employed as free particles dispersed throughout the pharmaceutical formulation or, in a preferred embodiment, dispersed throughout the polymer matrices in polymer-based formulations.

The pharmaceutical formulations of the present invention include an effective amount of biologically active agent. An effective amount of a biologically active agent is a therapeutically, prophylactically or diagnostically effective amount, which can be determined by a person of ordinary skill in the art taking into consideration factors such as route of administration; body weight; age; physical condition; therapeutic, prophylactic or diagnostic goal; and type of biologically active agent.

In the case of polymer-based formulations, the type of polymer used, initial burst and subsequent release levels desired, and desired release rate can also influence the amount of a biologically active agent that produces the desired effect. Initial and subsequent release levels, as well as release rates, are known for a number of polymeric matrices. These parameters can also be determined empirically by comparative in vitro tests of polymeric matrices containing different concentrations of one or more biologically active agents. Typically, a polymeric matrix intended to modulate the release of a biologically active agent contains from about 0.01 percent (w/w) biologically active agent to about 50 percent biologically active agent (w/w).

Where the biologically active agent is a polypeptide, preferred pharmaceutical formulations of the invention include a metal cation component. In polymer-based formulations, the metal cation component is preferably mixed with the agent prior to addition to the polymeric matrix. The metal cation component is selected such that it modulates the release of the polypeptide from the polymeric matrix. A suitable metal cation component has at least one kind of multivalent metal cation (having a valence of +2 or more) in a non-dissociated state, a dissociated state, or a combination of non-dissociated and dissociated states. Suitable metal cation components include, for instance, metal salts, metal hydroxides, and basic (pH of about 7.0 or higher) salts of weak acids, wherein the salt contains a metal cation. An exemplary metal cation component is zinc derived from zinc acetate (See Example 1.)

Pharmaceutical formulations according to the invention are produced by adding the particulate/biologically active agent component(s) to an injection vehicle according to the invention. For polymer-based formulations, polymeric microparticles including the biologically active agent are added to the injection vehicle.

To form such polymeric microparticles, a suitable polymer is dissolved in a solvent to form a polymer solution. Examples of suitable solvents include, for instance, polar organic solvents such as methylene chloride, dichloromethane, chloroform, tetrahydrofuran, dimethyl sulfoxide, and hexafluoroisopropanol. Suitable polymer solutions generally contain about 5 percent to about 30 percent polymer (w/v). In a more preferred embodiment, the polymer solution contains about 5 to about 15 percent polymer (w/v).

At least one biologically active agent is dispersed within the polymer solution. The biologically active agent can be dispersed by any suitable method that produces a relatively homogeneous suspension or solution, including sonication, mixing, and homogenization. A biologically active agent can be added directly to the polymer solution as a solid, preferably in particulate form. In the latter case, the biologically active agent typically becomes suspended as solid particles dispersed within the polymer solution. In some embodiments, before addition to a polymer solution, the biologically active agent is conveniently suspended as solid particles or dissolved in a second solvent, and the resulting solution is then added to the polymer solution. The second solvent can be the same as first solvent (i.e., that used to dissolve the polymer) or, alternatively, can be a different solvent, provided the second solvent is miscible with the first solvent, and the polymer is soluble in the second solvent. An example of a suitable second solvent is acetone. Those skilled in the art appreciate that the biologically active agent can also be suspended or dissolved in a solvent, after which, a suitable polymer or polymer solution is added to the biologically active agent suspension or solution.

In a preferred embodiment, a metal cation component is added to the polymer solution. The metal cation component and biologically active agent can be added to the polymer solution sequentially, in reverse order, intermittently, or through separate, concurrent additions. In one embodiment, the metal cation component is dissolved in a solvent, which is also suitable for the polymer and then mixed into the polymer solution. Alternatively, the biologically active agent can be added to a metal cation component suspension or solution (or vice versa), followed by addition of the polymer.

The metal cation component is employed in a concentration that modulates the release of a biologically active agent. The concentration selected depends upon the polymer, the metal cation component, and the biologically active agent utilized. In one embodiment, a metal cation component is dispersed in the polymeric matrix at a concentration between about 0.5 percent and about 30 percent (w/w). In a preferred embodiment, the metal cation component concentration is between about 1 percent (w/w) and about 10 percent (w/w).

The polymeric matrix of this invention can be formed into any shape suitable for injections, such as a microparticle. A microparticle can have a spherical (i.e., generally rounded), non-spherical or irregular shape. However, the preferred microparticle shape is a sphere. Preferred microparticles have an average diameter of between about 5 and about 200 microns.

A microparticle can be produced from polymeric solutions such as those described above by any of a number of available methods. Suitable methods for forming a microparticle from a polymer solution are described in U.S. Pat. No. 5,019,400 issued to Gombotz et al.; PCT Application No. PCT/US95/05511, Publication No. WO 95/29664; and in Example 1. In another embodiment, microparticles are prepared by the solvent evaporation method described in U.S. Pat. No. 3,737,337, issued to Schnoring et al.; U.S. Pat. No. 3,523,906, issued to Vranchen et al.; U.S. Pat. No. 3,691,090, issued to Kitajima et al.; or U.S. Pat. No. 4,389,330, issued to Tice et al. Other exemplary methods for forming microparticles are described in U.S. Pat. No. 5,643,605, issued to Cleland et al.

In the solvent evaporation method, a polymer solution, which contains a dispersed biologically active agent, and optionally a dispersed metal cation component, is mixed with a continuous phase, in which the polymer solution is substantially immiscible, to form an emulsion. The continuous phase is usually an aqueous solvent. Emulsifiers are often included in the continuous phase to stabilize the emulsion. The polymer's solvent is then evaporated over a period of several hours or more, thereby solidifying the polymer to form a polymeric matrix in microparticle form.

Pharmaceutical formulations according to the invention can include other components, such as a physiologically acceptable excipient or stabilizer. A physiologically acceptable excipient, or stabilizer suitable for use in the invention is non-toxic to recipients at the dosages employed, and can include an antioxidant (e.g., ascorbic acid), a low-molecular weight (less than about 10 residues) polypeptide, a protein (such as serum albumin, gelatin, and an immunoglobulin), a hydrophilic polymer (such as polyvinylpyrrolidone), an amino acid (such as glycine, glutamine, asparagine, arginine, and lysine), a monosaccharide, a disaccharide, polysaccharide and other carbohydrates (including glucose, mannose, dextrins, celluloses and methylcellulose), a chelating agent (e.g., ethylenediaminetetraacetic acid [EDTA]), a sugar alcohol (such as mannitol and sorbitol), a salt-forming counterion (e.g., sodium), a metal cation (e.g., zinc), an anionic surfactant (such as Tween™, Pluronics™, and PEG) and/or a preservative (e.g., those containing quaternary ammonium salts, such as benzethonium chloride).

Excipients or stabilizers can be dispersed within a polymeric matrix as described above for the optional metal cation component, provided that any such excipient or stabilizer does not significantly interfere with the formation of the polymeric matrix. Excipients or stabilizers can also be added to the injection vehicle.

Preferred sustained-release formulations for polypeptides can include polypeptides attached, typically via ε-amino groups, to a polyalkylene glycol (e.g., polyethylene glycol [PEG]). Attachment of PEG to proteins is a well-known means of reducing immunogenicity and extending in vivo half-life (see, e.g., Abuchowski, J., et al. (1977), J. Biol. Chem. 252:3582-86). Any conventional "pegylation" method can be employed, provided the "pegylated" polypeptide retains at least one biological activity.

Pharmaceutical formulations of the invention can be stored in any standard form, including, for example, an aqueous solution or a lyophilized cake. Such formulations are typically sterile when administered to recipients. Sterilization of an aqueous solution is readily accomplished by filtration through a sterile filtration membrane. If the formulation is stored in lyophilized form, the formulation can be filtered before lyophilization and reconstitution.

The invention also provides articles of manufacture including injection vehicles and formulations according to the invention as well as related kits. The invention encompasses any type of article including an injection vehicle or formulation of the invention, but the article of manufacture is typically a container, preferably bearing a label identifying the injection vehicle or formulation contained therein. The container can be formed from any material that does not react with the contained injection vehicle or formulation and can have any shape or other feature that facilitates use of the injection vehicle or formulation for the intended application. A container for an injection vehicle or pharmaceutical formulation of the invention generally has a sterile access port, such as, for example, an intravenous solution bag or a vial having a stopper pierceable by a hypodermic injection needle.

Kits of the invention generally include one or more such articles of manufacture and preferably include instructions for use.

Administration of Polymeric Formulations

The formulations of this invention can be administered to an animal, preferably a mammal, more preferably a human, by injection. Suitable routes of administration include, for example, intravenous, intraperitoneal, intracerebral, intramuscular, intraocular, intravitreal, intraarterial, subcutaneous, or intralesional routes. Pharmaceutical formulations of the invention can be administered continuously by infusion, by bolus injection, or by any injection method appropriate for the particular preparation.

The needle employed for injection should have a bore size that allows injection of the desired dose of the pharmaceutical formulation. Generally, a 23 gauge needle provides good injectability of polymer-based formulations, but smaller (e.g., 24, 25, 26, 27, and 28 gauge) needles are preferred to reduce the pain of injection.

Dosages for pharmaceutical formulations according to the invention depend on a variety of considerations, such as the therapeutic objectives, the route of administration, and the condition of the recipient, and the maximum dose that can be administered by injection. Accordingly, it is necessary for the clinician to titer the dosage and modify the route of administration as required to obtain the optimal therapeutic effect. A typical daily dosage can range from about 1 μg/kg up to about 100 mg/kg of body weight or more per day, but is typically between about 10 μg/kg/day to 10 mg/kg/day. Generally, the clinician begins with a low dosage of a pharmaceutical formulation and increases the dosage until the desired therapeutic effect is achieved.

The administration of a pharmaceutical formulation of the invention can be combined with other therapeutic regimens. For the treatment of cancer, radiation and/or a chemotherapeutic agent can be administered concomitantly with a pharmaceutical formulation of the invention. Suitable preparation and dosing schedules for chemotherapeutic agents are as recommended by the manufacturer or as determined empirically by the clinician. Preparation and dosing schedules for standard chemotherapeutic agents are found in Chemotherapy Service Perry ed., (Williams & Wilkins (1992)). The chemotherapeutic agent can be administered before, after, or simultaneously with administration of the pharmaceutical formulation. Antibodies against tumor-associated antigens, such as antibodies that bind EGFR, ErbB-2, ErbB-3, or ErbB-4 receptor, or vascular endothelial growth factor (VEGF) can also be co-administered with a pharmaceutical formulation(s) of the invention, as can one or more cytokines.

EXAMPLES

Example 1

Preparation of Polymeric Microspheres Containing Recombinant Human Growth Hormone Recombinant human growth hormone (rhGH) was encapsulated into PLGA microspheres using a cryogenic, non-aqueous process described by Gombotz et al., U.S. Pat. No. 5,019,400, issued in 1991. To stabilize rhGH, the protein was formulated with zinc acetate to produce a sparingly soluble Zn:rhGH complex. Zinc was chosen because histochemical evidence indicated that hGH is stored in the pituitary as a zinc complex. In addition, rhGH complexed with zinc was known to be more resistant than uncomplexed rhGH to denaturation with guanidine hydrochloride.

Eleven different microsphere formulations were made for initial evaluation. The variables that were investigated were polymer molecular weight (10 kD, 8 kD, and 31 kD), polymer end group (capped or uncapped), and the amount of zinc carbonate (0, 1, 3, and 6%) added as an excipient. The zinc carbonate excipient was included to act as a depot for zinc ions to ensure that rhGH remained complexed to zinc. The molar ratio of lactide to glycolide in all polymers was kept constant at 50:50, and the molar ratio of Zn:rhGH in all microsphere formulations investigated was 6:1. All microsphere formulations were prepared using D,L-PLGA obtained either from Birmingham Polymers (Birmingham, Ala.; #115-56-1; 0.2 dL/g, 1 D, dodecanyl end group [i.e., capped,]) or from Boehringer Ingelheim (Ingelheim, Germany; RG502H, 0.2 dL/g, 8 kD; and RG503H, 0.4 dL/g, 31 cD, both of which had a carboxylic and acid end group [i.e., uncapped]).

Microspheres were produced as described in Johnson, O., et al.; *Pharmaceutical Research*, "The Stabilization and Encapsulation of Human Growth Hormone into Biodegradable Microspheres," Vol. 14, No. 6 (1997). Briefly, rhGH was first formulated into a lyophilized powder, and the lyophilized powder was then encapsulated into the microspheres. Lyophilized powder was prepared by mixing solutions of rhGH (Nutropin, Genentech, Inc.) with zinc acetate to achieve a molar ratio of 6:1 zinc acetate:rhGH. The Zn:rhGH dispersion was atomized through an ultrasonic nozzle into liquid nitrogen, and the frozen droplets were lyophilized.

The polymer suspension was sprayed through a sonicating nozzle into a vessel containing frozen ethanol overlaid with liquid nitrogen. The vessel was then transferred to −80° C., where the ethanol melted, and the microspheres hardened as the dichloromethane was extracted by the ethanol. After 3 days, the microspheres were harvested by filtration, dried under vacuum, and sieved through a 106 μm mesh screen.

Example 2

Analysis of rhGH Microspheres

The eleven microsphere formulations of Example 1 were analyzed using a variety of techniques. Microspheres were placed on an aluminum stub and sputter coated with a layer of carbon or gold and imaged using a JEOL model 6400 scanning electron microscope. The mean particle diameter distribution of the microspheres was determined using a Coulter Multisizer. The rhGH load of the microspheres was determined by nitrogen analysis.

Approximately 95% of protein was encapsulated into microspheres, which had a mean volume diameter of about 50 microns.

In addition, the physical and biological integrity of the rhGH recovered from the microspheres was analyzed by size exclusion (SEC), reversed-phase, and anion-exchange chromatography. These techniques were used to detect aggregated, oxidized, and deamidated rhGH respectively. For these analyses, rhGH was recovered from the microspheres using two different methods. In the first, the microspheres were dissolved in a mixture of methylene chloride and acetone, and the protein precipitate was collected. In the second, the protein was recovered by incubating the microspheres in HEPES buffer.

Chromatography was done according to published methods (Teshima, G., and Canoval-Davis, E. (1991), J. Biol. Chem. 266:13544-47; Battersby, J. E., et al. (1992), J. of Chromatog. 625:2007-15; Battersby, J. E., et al. (1995) Anal. Chem. 67:447-55; Canova-Davis, E., et al. (1990), Int. J. Peptide Protein Res. 35:17-24). Briefly, SEC was performed on a G2000SW XL TSK Gel Column with phosphate buffer as the mobile phase. rhGH was detected by UV absorption at 214 nm. Reversed-phase chromatography was carried out on a polymeric reversed-phase column using acetonitrile gradient elution at 50° C. Ion-exchange chromatography was performed on a DEAE-5PW TSK Gel Column with a phosphate and acetonitrile gradient elution. For the reversed phase and ion-exchange methods, rhGH was detected by fluorescence, with excitation at 286 nm and emission at 335 nm.

Finally, rhGH bioactivity was determined in a cell proliferation assay using a cell line that expresses the receptor for hGH and proliferates in the presence of hGH (see Roswall, E. C., et al. (1996) Biologicals 24:25-39). Cell proliferation was measured by conversion of Alamar Blue dye to a fluorescent product by intracellular reductases. Fluorescence is proportional to the number of cells. rhGH-containing samples were incubated with cells for 72 hours at 37° C., and fluorescence, was quantitated.

The rhGH recovered from each of the formulations was essentially monomeric, indicating that there was no effect of the formulation variables tested on protein aggregation. The analysis of rhGH integrity indicated that there were no significant differences between the protein before and after encapsulation. In addition, the specific bioactivity of the protein released from all formulations analyzed was similar to that of the unencapsulated standard. Furthermore, SDS-reducing gel electrophoresis and HPLC analysis of a tryptic digest of one of the formulations revealed that the extracted protein was comparable to unencapsulated protein. Taken together, these data show that rhGH is essentially unaltered after extraction or release from microspheres after extended incubation at physiological temperatures.

Example 3

Syringebility Study of an anti-VEGF Fab Polymer-Based Formulation Containing Sodium Hyaluronate (Amvisc® Plus)

An injection vehicle was prepared by diluting Amvisc® Plus (Chiron Vision Corporation, Claremont, Calif., USA) in 0.9% Sodium Chloride USP.

Amvisc® Plus is supplied in a disposable glass syringe delivering either 0.4 mL or 0.8 mL of 1.6% sodium hyaluronate (w/v) in physiological saline. Each mL of Amvisc® Plus contains 16 mg of sodium hyaluronate, 9 mg NaCl dissolved in sterile water for injection (SWFI USP). Amvisc® Plus was diluted to 0.05%, 0.1%, 0.2%, 0.4%, 0.6%, and 0.8% (i.e., 0.5,1,2,4,6, and 8 mg/ml).

The injection vehicles were mixed with anti-VEGF Fab PLGA microspheres prepared as described in Example 1 to produce formulations containing 100 mg/mL anti-VEGF Fab PLGA microspheres (lot 96-22-195-1).

These formulations were tested for syringebility by injecting 1 mL of each formulation into tubes using 23, 24, 25, 27, and 28 gauge needles. 1 mL of each formulation was readily injectable through all needles tested.

A similar polymer-based formulation using a 3.0% (w/v) solution of the linear carbohydrate carboxymethyl cellulose (CMC) as the injection vehicle required a 21 gauge needle for injection of a 100 mg/mL dose.

Example 4

Syringebility Study of Various Polymer-Based Formulations Containing Sodium Hyaluronate (Amvisc® Plus)

An injection vehicle was prepared by diluting Amvisc® Plus (Chiron Vision Corporation, Claremont, Calif., USA) in 0.9% Sodium Chloride USP to 0.05%, 0.1%, 0.15%, and 0.2% (w/v).

To produce polymer-based formulations, the injection vehicle was mixed with Nutropin Depot VEGF microspheres, VEGF/heparin microspheres, and NGF microspheres. These microsphere preparations were prepared as described in Example 1. The microsphere concentrations are given in Table 1.

These formulations were tested for syringebility by injecting 1 mL of each formulation into tubes using 23, 24, 25, 27, and 28 gauge needles. The results of this study are shown in Table 1, which indicates the smallest gauge needle that could be used to inject 1 mL of each formulation.

TABLE 1

| Products Tested | Amvisc® Plus Concentration | | | |
|---|---|---|---|---|
| | 0.05% | 0.1% | 0.15% | 0.2% |
| Nutropin Depot® (lot ASO-b, 125 mg/mL, Alkermes) | ≦25 G* | ≦24 G | ≦24 G | ≦24 G |
| VEGF microspheres (lot VEGF-18, 100 mg/mL, Genentech) | ≦24 G | ≦24 G | ≦24 G | ≦23 G |
| VEGF/heparin microspheres (lot VEGF-22, 100 mg/mL, Genentech) | ≦24 G | ≦24 G | ≦24 G | ≦23 G |
| NGF microspheres (lot NGF-14, 100 mg/mL, Genentech) | ≦25 G | ≦25 G | ≦24 G | ≦24 G |

*Indicates that the formulation could be injected through 25 gauge or larger (smaller G) needles.

Example 5

Syringebility Study of Various Polymer-Based Formulations Containing Sodium Hyaluronate (Hylumed®)

An injection vehicle containing sodium hyaluronate was prepared by diluting Hylumed® (Genzyme Pharmaceuticals, Cambridge, Mass., USA) to 0.01% and 0.10% in 0.9% Sodium Chloride USP. For comparison, a second vehicle containing 3% (w/v) carboxymethylcellulose (CMC) in 0.9% Sodium Chloride USP was also prepared.

The injection vehicles were mixed with the microsphere preparations indicated in Table 2, which were prepared as described in Example 1. The microsphere concentrations are given in Table 2.

These formulations were tested for syringebility by injecting 1 mL of each formulation into tubes using 21, 22, 23, 24, 25, 26 and 27 gauge needles. The results of this study are shown in Tables 2 and 3, which indicates the smallest gauge needle that could be used to inject each formulation. Table 3 indicates that when the microsphere concentration is doubled for formulations containing 0.10% Hylumed®, a small (24 G) gauge needle can be employed for injection. Thus, a smaller gauge needle can be used to inject twice as many microspheres in one dose as with a conventional CMC-based injection vehicle.

TABLE 2

| Products Tested | Hylumed® Conc. | | CMC Conc. |
|---|---|---|---|
| | 0.01% | 0.10% | 3.0% |
| Nutropin Depot® (lot ASO-b, 125 mg/mL, Alkermes) | ≦24 G* | ≦25 G | ≦22 G |
| Nutropin Depot® (lot 3000511, 125 mg/mL, Alkermes) | ≦24 G | ≦25 G | ≦22 G |
| Nutropin Depot® (lot 541a, 125 mg/mL, Alkermes) | ≦24 G | ≦24 G | ≦22 G |
| VEGF microspheres (lot VEGF-20, 100 mg/mL, Genentech) | ≦24 G | ≦25 G | ≦22 G |

*Indicates that the formulation could be injected through 24 gauge or larger (smaller G) needles.

TABLE 3

| Products Tested | Hylumed® Concentration 0.10% |
|---|---|
| Nutropin Depot® (lot ASO-b, 250 mg/mL, Alkermes) | ≦24 G* |

TABLE 3-continued

| Products Tested | Hylumed ® Concentration 0.10% |
|---|---|
| Nutropin Depot ® (lot 3000511, 250 mg/mL, Alkermes) | ≦24 G |
| Nutropin Depot ® (lot 541a, 250 mg/mL, Alkermes) | ≦24 G |
| VEGF microspheres (lot VEGF-20, 200 mg/mL, Genentech) | ≦24 G |

*Indicates that the formulation could be injected through 25 gauge or larger (smaller G) needles.

Example 6

Suitability of Various Macromolecules for Use in an Injection Vehicle for Polymer-Based Microspheres Solutions of the following macromolecules in 0.9% Sodium Chloride USP were prepared for use as injection vehicles for polymer-based microspheres:sodium alginate (Kelco Co., San Diego, Calif., USA), aggrecan (Sigma Chemical Co., St. Louis, Mo., USA), dextran 70 (Sigma Chemical Co., St. Louis, Mo., USA), jeffamine M-600 (Hampton Res., Laguna Niguel, Calif., USA), jeffamine ED-2001 (Hampton Res., Laguna Niguel, Calif., USA), keretan sulphate (Sigma Chemical Co., St. Louis, Mo., USA), laminin (Sigma Chemical Co., St. Louis, Mo., USA), poly-L-ornithine (Sigma Chemical Co., St. Louis, Mo., USA), xanthan gum (Sigma Chemical Co., St. Louis, Mo., USA), and gellan gum (Sigma Chemical Co., St. Louis, Mo., USA).

Concentrations tested ranged from 0.01%-1.0% (w/v). Nutropin Depot® microspheres, prepared as described in Example 1, were added to a final concentration of 125 mg/mL.

These formulations were tested for syringebility by injecting 1 mL of each formulation into tubes using 21, 22, 23, 24, 25, 26 and 27 gauge needles. The results of this study indicated that a 21 G needle is the smallest gauge needle that could be used to inject 1 mL of each formulation. Thus, none of the vehicles tested were superior to conventional CMC-based vehicles.

Example 7

Intravitreal Injectability Study of Polymer-Based Formulations Containing Anti-VEGF Fab in Sodium Hyaluronate Two injection vehicles were prepared, the first, from Amvisc® Plus (Chiron Vision Corporation, Claremont, Calif., USA) and the second, from sodium hyaluronate obtained from Sigma Chemical Company, (St. Louis, Mo.). Both were diluted to 0.1% (w/v) sodium hyaluronate in 0.9% Sodium Chloride USP.

To produce polymer-based formulations, each injection vehicle was mixed with anti-VEGF Fab microspheres (100 mg/mL). The microspheres were prepared as described in Example 1.

These formulations were tested for intravitreal injectability into the eyes of rabbits. 50 μL of each formulation was readily injectable using a 30 gauge needle. No significant inflammation was observed in the rabbits' eyes 24 hours after injection.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

All references cited herein are expressly incorporated by reference.

What is claimed is:

1. A method for administering a biologically active agent, the method comprising:
   injecting to an animal a formulation comprising:
   (a) an injection vehicle comprising hyaluronic acid or sodium hyaluronate dissolved in a physiological buffer at a concentration of about 0.01 to about 3 percent weight per volume; and
   (b) particles comprising:
       (i) a first component that is the biologically active agent; and
       (ii) a second component that is a biocompatible polymeric matrix,
   wherein the concentration of the particles is about 100 mg/mL to about 500 mg/mL of the formulation, and further wherein the hyaluronic acid or sodium hyaluronate is at a concentration sufficient to inject the formulation through a 23-gauge or smaller bore needle.

2. The method of claim 1, wherein the concentration of hyaluronic acid or sodium hyaluronate is about 0.01 to about 1 percent weight per volume.

3. The method of claim 2, wherein the concentration of hyaluronic acid or sodium hyaluronate is about 0.01 to about 0.8 percent weight per volume.

4. The method of claim 1, wherein the injection vehicle comprises hyaluronic acid.

5. The method of claim 1, wherein the hyaluronic acid or sodium hyaluronate is at a concentration sufficient to inject the formulation through a 24-gauge needle.

6. The method of claim 1, wherein the hyaluronic acid or sodium hyaluronate is at a concentration sufficient to inject the formulation through a 25-gauge needle.

7. The method of claim 1, wherein the hyaluronic acid or sodium hyaluronate is at a concentration sufficient to inject the formulation through a 26-gauge needle.

8. The method of claim 1, wherein the hyaluronic acid or sodium hyaluronate is at a concentration sufficient to inject the formulation through a 27-gauge needle.

9. The method of claim 1, wherein the hyaluronic acid or sodium hyaluronate is at a concentration sufficient to inject the formulation through a 28-gauge needle.

10. The method of claim 1, wherein the hyaluronic acid or sodium hyaluronate is at a concentration sufficient to inject the formulation through a 30-gauge needle.

11. An injectable formulation, comprising:
   (a) an injection vehicle comprising hyaluronic acid or sodium hyaluronate dissolved in a physiological buffer at a concentration of about 0.01 to about 3 percent weight by volume; and
   (b) particles, comprising:
       (i) a first component that is a biologically active agent, and
       (ii) a second component that is a biocompatible polymeric matrix,
   wherein the concentration of the particles is about 100 mg/mL to about 500 mg/mL of the formulation, and further wherein the hyaluronic acid or sodium hyaluronate is at a concentration sufficient to inject the particles through a 23-gauge or smaller bore needle.

12. The injectable formulation of claim 11, wherein the physiological buffer comprises physiological saline.

13. The injectable formulation of claim 11, wherein the polymeric matrix comprises a blocked polymer.

14. The injectable formulation of claim 11, wherein the polymeric matrix comprises an unblocked polymer.

15. The injectable formulation of claim 11, wherein the polymeric matrix comprises poly(lactide-co-glycolide).

16. The injectable formulation of claim 11, wherein the biologically active agent is a polypeptide.

17. The injectable formulation of claim 16, wherein the polypeptide is selected from the group consisting of a growth hormone, a cytokine; a cytokine receptor: a chimeric protein comprising a cytokine or its receptor; a tumor necrosis factor; a tumor necrosis factor receptor; a lipoprotein; a clotting factor: an anti-clotting factor; a serum albumin; a microbial protein; a receptor for a hormone; a receptor for a growth factor; a rheumatoid factor; a neurotrophic factor; a nerve growth factor; a fibroblast growth factor; a transforming growth factor (TGF); a CD protein; an osteoinductive factor; an immunotoxin; a bone morphogenetic protein (BMP); an interferon; a colony stimulating factor (CSF); an interleukin (IL); a viral antigen; a transport protein; a homing receptor; a regulatory protein; an antibody; a chimeric protein, a plasminogen activator; a tissue-type plasminogen activator; a urokinase; an insulin-like growth factor binding protein; a T-cell receptor; a surface membrane protein; an HIV-1 envelope glycoprotein; and an immunoadhesin.

18. The injectable formulation of claim 16, wherein the polypeptide is an anti-vascular endothelial growth factor Fab (anti-VEGF Fab).

19. The injectable formulation of claim 16, wherein the polypeptide is selected from the group consisting of tumor necrosis factor-alpha (TNF-alpha); tumor necrosis factor-beta (TNF-beta); tumor necrosis factor receptor-1 (TNFR-1); tumor necrosis factor receptor-2 (TNFR-2); renin; human growth hormone; bovine growth hormone; growth hormone releasing factor; parathyroid hormone; thyroid stimulating hormone; alpha-1-antitrypsin; insulin A-chain; insulin B-chain; proinsulin; follicle stimulating hormone; calcitonin; luteinizing hormone; glucagon; factor VIIIC; factor IX; tissue factor; von Willebrand's factor; Protein C; atrial natriuretic factor; lung surfactant; bombesin; thrombin; hemopoietic growth factor; enkephalinase; RANTES; human macrophage inflammatory protein (MIP- 1-alpha); human serum albumin; mullerian-inhibiting substance; relaxin A-chain; relaxin B-chain; prorelaxin; mouse gonadotropin-associated peptide; beta-lactamase; DNase; inhibin; activin; vascular endothelial growth factor (VEGF); anti-VEGF Fab; glucagon-like peptide I (GLP-I); hepatocyte growth factor (HGF); integrin; protein A; protein D; bone-derived neurotrophic factor (BDNF); neurotrophin-3, -4, -5, and -6 (NT-3, NT-4, NT-5, NT-6); NGF-beta; platelet-derived growth factor (PDGF); aFGF; bFGF; epidermal growth factor (EGF); TGF-alpha; TGF-beta, including TGF-beta1, TGF-beta2, TGF-beta3, TGF-beta4, and TGF- beta5; insulin-like growth factor-I (IGF-I); insulin-like growth factor-II (IGF-II); des (1-3)-IGF-I (brain IGF-I); CD-3; CD-4; CD-8; CD-19; erythropoietin; interferon-alpha; interferon-beta; interferon-gamma; M-CSF; GM-CSF; G-CSF; IL-1; IL-2; IL-3; IL-4; IL-5; IL-6; IL-7; IL-8; IL-9; IL-10; superoxide dismutase; decay accelerating factor; gp120; gp160; and addressin.

20. The injectable formulation of claim 11, wherein the concentration of the particles in the formulation is about 100 mg/mL to about 300 mg/mL.

21. The injectable formulation of claim 11, wherein the injection vehicle comprises hyaluronic acid.

22. The injectable formulation of claim 11, wherein the injection vehicle comprises sodium hyaluronate.

23. The injectable formulation of claim 11, wherein the concentration of hyaluronic acid or sodium hyaluronate is about 0.01 to about 1 percent weight per volume.

24. The injectable formulation of claim 23, wherein the concentration of hyaluronic acid or sodium hyaluronate is about 0.01 to about 0.8 percent weight per volume.

25. The injectable formulation of claim 23, wherein the concentration of hyaluronic acid or sodium hyaluronate is between about 0.05 and about 1 percent weight per volume.

26. The injectable formulation of claim 23, wherein the concentration of hyaluronic acid or sodium hyaluronate is between about 0.05 and about 0.8 percent weight per volume.

27. The injectable formulation of claim 11, wherein the polymeric matrix comprises a polymer selected from a biodegradable polymer, a non-biodegradable polymer, a mixture of biodegradable and non-biodegradable polymers, and a copolymer comprising biodegradable and non-biodegradable units.

28. The injectable formulation of claim 11, wherein the polymeric matrix comprises a polymer selected from blocked polymers, unblocked polymers, and mixtures of blocked and unblocked polymers.

29. The injectable formulation of claim 11, wherein the polymeric matrix comprises a polymer selected from a poly (glycolide); a poly (lactide-co-glycolide); a poly (lactic acid); a poly (glycolic acid); a poly (lactic acid-co-glycolic acid); a polyanhydride; a polyorthoester; a polyetherester; a polycaprolactone; a polyesteramide; a block copolymer of polyethylene glycol and lactide; a block copolymer of polyethylene glycol and glycolide; and blends or copolymers thereof.

30. A method for administering the injectable formulation of claim 11, the method comprising injecting the injectable formulation through a 23-gauge or smaller bore needle.

31. The injectable formulation of claim 11, wherein the biologically active agent is dispersed within, coated on, or dispersed within and coated on the particles.

32. The injectable formulation of claim 31, wherein the biologically active agent is dispersed within the particles.

33. The injectable formulation of claim 11, wherein the particles are microparticles.

34. The injectable formulation of claim 11, wherein the particles are microspheres.

35. The injectable formulation of claim 11, wherein the particles have an average diameter of between about 5 and about 200 microns.

36. The injectable formulation of claim 11, wherein the concentration of particles in the formulation is between about 125 mg/mL to about 250 mg/mL.

37. The injectable formulation of claim 11, wherein the concentration of particles in the formulation is between about 200 mg/mL to about 250 mg/mL.

38. The injectable formulation of claim 11, wherein the hyaluronic acid or sodium hyaluronate is at a concentration sufficient to inject the formulation through a 24-gauge needle.

39. The injectable formulation of claim 11, wherein the hyaluronic acid or sodium hyaluronate is at a concentration sufficient to inject the formulation through a 25-gauge needle.

40. The injectable formulation of claim 11, wherein the hyaluronic acid or sodium hyaluronate is at a concentration sufficient to inject the formulation through a 26-gauge needle.

41. The injectable formulation of claim 11, wherein the hyaluronic acid or sodium hyaluronate is at a concentration sufficient to inject the formulation through a 27-gauge needle.

42. The injectable formulation of claim 11, wherein the hyaluronic acid or sodium hyaluronate is at a concentration sufficient to inject the formulation through a 28-gauge needle.

43. The injectable formulation of claim 11, wherein the hyaluronic acid or sodium hyaluronate is at a concentration sufficient to inject the formulation through a 30-gauge needle.

44. A method for making a pharmaceutical formulation, comprising:
  adding an effective amount of a biologically active agent coated on, dispersed within, or coated on and dispersed within polymeric particles to an aqueous injection vehicle comprising hyaluronic acid or sodium hyaluronate at a concentration of about 0.01 to about 3% (w/v);
  wherein the concentration of particles in the formulation is between about 100 and 500 mg/mL (w/v); and further wherein the hyaluronic acid or sodium hyaluronate is at a concentration sufficient to inject the particles through a 23-gauge or smaller bore needle.

* * * * *

UNITED STATES PATENT AND TRADEMARK OFFICE
CERTIFICATE OF CORRECTION

| | | |
|---|---|---|
| PATENT NO. | : 7,582,311 B1 | Page 1 of 1 |
| APPLICATION NO. | : 09/687951 | |
| DATED | : September 1, 2009 | |
| INVENTOR(S) | : Jeffrey L. Cleland et al. | |

It is certified that error appears in the above-identified patent and that said Letters Patent is hereby corrected as shown below:

In the Specification:

- In column 7, line 20, please replace "erythrbpoietin" with --erythropoietin--.

- In column 11, line 45, please replace "1 D" with --10kD--.

- In column 11, line 49, please replace "cD" with --kD--.

- In column 13, line 43, please replace "Nutropin Depot" with --Nutropin Depot®--.

- In column 15, line 24, please replace "microspheres:sodium" with --microspheres: sodium--.

In the Claims:

- In column 17, line 61, please replace "TGF- beta5" with --TGF-beta5--.

Signed and Sealed this

Twenty-ninth Day of June, 2010

David J. Kappos
*Director of the United States Patent and Trademark Office*